United States Patent [19]

Foglio et al.

[11] 4,036,835
[45] July 19, 1977

[54] PROCESS FOR PREPARING CEPHALOSPORINS

[75] Inventors: Maurizio Foglio; Giovanni Franceschi, both of Paolo Masi; Antonino Suarato, Milan, all of Italy

[73] Assignee: Societa' Farmaceutici Italia, Milan, Italy

[21] Appl. No.: 662,338

[22] Filed: Mar. 1, 1976

Related U.S. Application Data

[63] Continuation-in-part of Ser. No. 578,875, May 19, 1975, abandoned.

[30] Foreign Application Priority Data

May 22, 1974 Italy .................................. 23070/74

[51] Int. Cl.² ...................................... C07D 501/02
[52] U.S. Cl. ................................ 260/243 C; 424/246
[58] Field of Search .................................. 260/243 C

[56] References Cited

U.S. PATENT DOCUMENTS

| | | | |
|---|---|---|---|
| 3,900,468 | 8/1975 | Martel et al. | 260/243 C |
| 3,900,487 | 8/1975 | Elphinstone | 260/243 C |
| 3,905,965 | 9/1975 | Martel et al. | |

*Primary Examiner*—Nicholas S. Rizzo
*Attorney, Agent, or Firm*—Stevens, Davis, Miller & Mosher

[57] ABSTRACT

A process for preparing cephalosporins of structure:

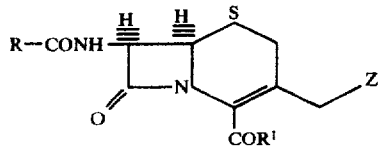

where R is hydrogen, $C_1$ to $C_4$ alkyl, cyano-methyl-, thienyl-methyl, furyl-methyl-, naphthyl-methyl-, phenyl-methyl-, phenoxy-methyl-, phenyl-isopropyl-, phenoxy-isopropyl-, pyridyl-4-thiomethyl-, and tetrazolyl-1-methyl;

$R^1$ is hydroxyl, $C_2$ to $C_4$ alkoxy, trichloroethoxy-, benzyloxy-, p-methoxy-benzyloxy-, p-nitrobenzyloxy-, benzhydryloxy-triphenylmethoxy-, phenacyloxy-, and p-halophenacyloxy;

Z is hydrogen, hydroxyl, —O—alkyl, —O—CO—alkyl, —Br, —I, —N₃, —NH₂, —O—CO—CH₃, —O—CO—NH₂ and an —S—mononuclear nitrogen heterocyclic ring;

wherein a compound of structure

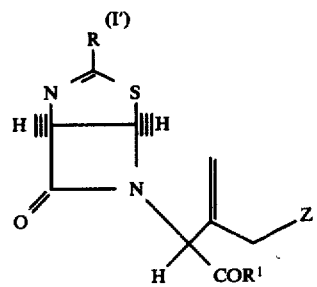

is reacted in a suitable solvent at a temperature between −20° C and +80° C, in the presence of an aqueous organic or inorganic acid with an azoderivative of the formula:

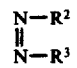

where $R^2$ and $R^3$ are equal or different and represent lower alkyl, a mononuclear aryl ring, CN—, a mononuclear heterocyclic ring, or the radicals —COR⁴, —COOR⁴,

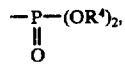

—CONHR⁴, or $R_2$ and $R_3$ together may represent the residues:

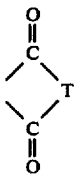 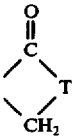

where T represents >CH₂, >N — R⁴, and

R⁴ is lower alkyl, a mononuclear aryl ring or a mononuclear heterocyclic ring, to give a compound of structure:

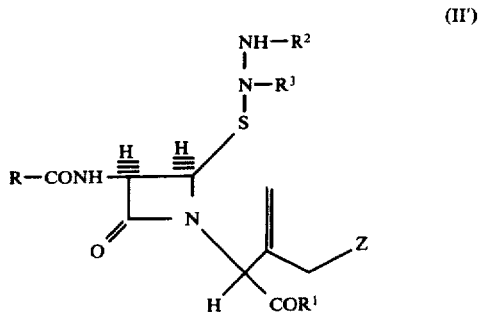

in which R, R¹, R², R³, and Z have the meanings given above, and said intermediate (II 40 ) is reacted in a suitable solvent at a temperature between −100° C and +120° C with a compound selected from the class consisting of inorganic bases, to finally give the desired compound (III) which is isolated and purified in known manner.

2 Claims, No Drawings

PROCESS FOR PREPARING CEPHALOSPORINS

This application is a continuation-in-part of our co-pending application Ser. No. 578,875, filed May 19, 1975, and now abandoned. See also our copending application Ser. No. 596,109, filed July 16, 1975, and now abandoned.

The present invention relates to a process for preparing cephalosporins.

More particularly, the invention relates to a new process for preparing cephalosporins starting from suitably substituted thiazoline-azetidinones.

The invention also relates to certain novel 2β-thiohydrazoazetidinones as intermediates.

The conversion step from the pencillanic structure to the cephalosporanic structure has been achieved chemically for the first time by treating sulphoxides of penicillins with acetic anhydride (R. R. Chauvette, J. Org. Chem. 36; 1971, p. 1259) or with acid catalysts (Belgian Patent No. 747,119). More recently, the transformation of sulphoxides of penicillins into cephalosporins, in the presence of azodicarboxylate, has been reported (S. Terao, Chem. Comm. 1304, 1972) with low yields and in admixture with other products.

The principal object of the present invention is to obtain cephalosporins by a completely novel process as indicated diagrammatically hereinafter:

THE SYNTHESIS DIAGRAM a. Opening of the thiazoline ring with an azoderivative:

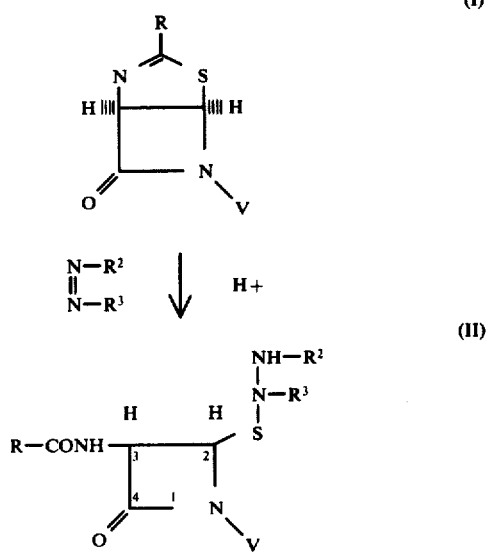

where, apart from the other substituents, V may be hydrogen, or an aliphatic, aromatic, arylaliphatic or acyl residue, and in particular the residues:

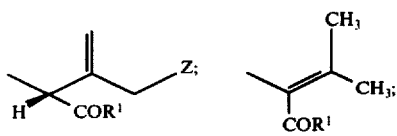

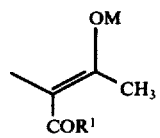

b. closure of the intermediate 2β-thiohydrazoazetidinone with inorganic oxides or bases

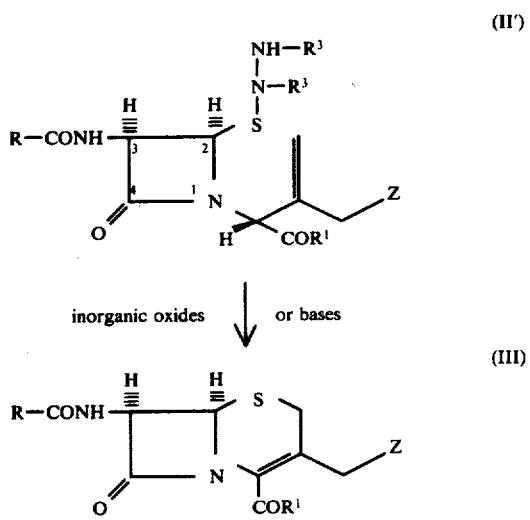

where R is selected from the class consisting of hydrogen, alkyl having from 1 to 4 carbon atoms, cyano-, methyl-, thienyl-methyl-, furyl-methyl-, naphthyl-methyl-, phenyl-methyl-, phenoxy-methyl-, phenyl-isopropyl-, pyridyl-4-thiomethyl-, and tetrazolyl-1-methyl-;

$R^1$ is selected from the class consisting of hydroxyl, alkoxy with 1 to 4 carbon atoms, trichloro-ethoxy-, benzyloxy-, p-methoxybenzyloxy-, p-nitrobenzyloxy-, benzhydryloxy-, triphenylmethoxy-, phenacyloxy-, and p-halophenacyloxy;

Z is selected from the class consisting of hydrogen, hydroxyl, —O—alkyl, —O—CO—alkyl, —Br, —I, —N₃, —NH₂, —O—CO—CH₂, —O—CO—NH₂, and an —S-mononuclear nitrogen heterocyclic ring;

M is hydrogen or an alkyl group with 1 to 4 carbon atoms; and $R^2$ and $R^3$ are as defined below.

The compound (I) may be obtained by heating the sulphoxide of penicillin in the presence of trialkylphosphite (See Neth. Pat. No. 70/08271).

The process of the present invention consists essentially in reacting the compound (I) in a suitable solvent at a temperature between −20° C and +80° C in the presence of an aqueous organic and inorganic acid with an azoderivative of the formula:

where $R^2$ and $R^3$ are equal or different and represent lower alkyl, a mononuclear aryl ring, CN-, a mononuclear heterocyclic ring, or the radicals —COR⁴, —COOR⁴,

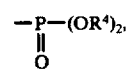

—CONHR⁴; or R₂ and R₃ together may represent the residues:

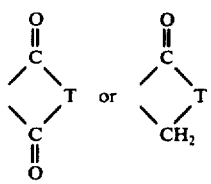

where T represents <CH₂, <N — R⁴, and

R⁴ is lower alkyl, a mononuclear aryl or a mononuclear heterocyclic ring.

The intermediate compound (II) is reacted in a suitable solvent and at a temperature between −100° C and +120° C with inorganic oxides such as Al₂O₃, Fe₂O₃, CR₂O₃, SiO₂, or with inorganic and organic bases such as KOH, Na₂CO₃, NH₄OH, alkali metal alcoholates, aliphatic, aromatic and heterocyclic amines, alkylammonium bases and basic resins.

In this manner the desired cephalosporin derivative (III) is obtained, which is then isolated and purified in per se known manner.

The following examples will serve to illustrate the invention without however limiting it.

EXAMPLE 1

Methyl-2β-thiohydrazodicarboxymethyl-α-isopropenyl-4-oxo-3β-phenoxyacetamido-1-azetidine acetate.

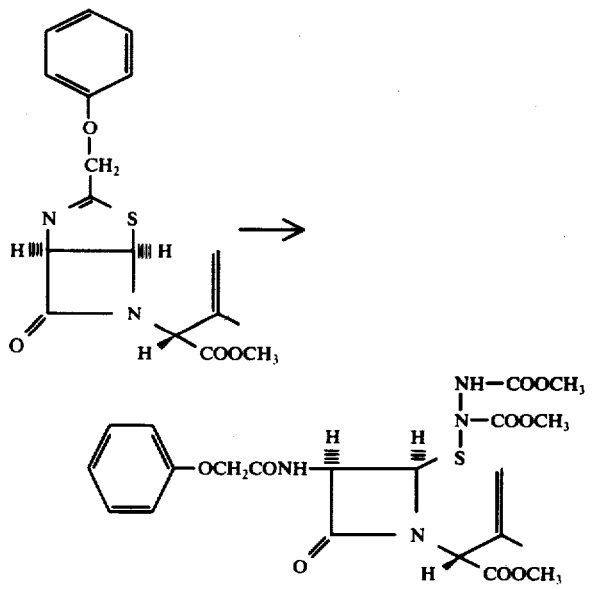

A solution of 5.0 g of methyl-α-isopropenyl-3-phenoxymethyl-1α,5α-4-thio-2,6-diaza-[3,2,0]-2-heptene-6-acetate-7-one in 200 ml of acetone containing 5 ml of methyl azodicarboxylate, 2.5 g of p-toluenesulphonic acid monohydrate, and 2.5 ml of water, is left at room temperature for 6-8 hours. This is then cooled to 0° C, and neutralised with a saturated solution of NaHCO₃.

The sodium salt of the p-toluenesulphonic acid which precipitates is filtered off and after evaporation of the acetone at room temperature, the residue is dissolved in methylene chloride and washed with salt water. The organic layer is dried over anhydrous Na₂SO₄ and evaporated. The residue is chromatographed over silica, eluting with 15% benzene-ethyl acetate.

In this way 6.2 g of methyl-2β-thiohydrazodicarboxymethyl-α-isopropenyl-4-oxo-3β-phenoxyacetamido-1-azetidine acetate are obtained; m.p. 133°- 135° C.

I.R. (CHCl₃): 3410 (N-H), 1775 (C = 0β-lactam) 1735 (C = 0 ester and carbamates) 1685 cm⁻¹(C = 0 amide)

N.M.R. (CDCl₃): 1.94 (singlet, 3H,

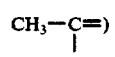

3.68, 3.73 and 3.81 (singlets, 9H, three COOCH₃), 4.56 (singlet, 2H, OCH₂CO), 4.90 (singlet, 1H,

N—CH—COOCH₃), 5.07 and 5.16 (widened singlets, 2H, =CH₂), 5.3 - 5.7 (multiplet, 2H, CH β lactam) and 6.9 - 8.0 δ (multiplet, 7H, aromatic H and NH).

Mass spectrum: m/ₑ 510 (M+) and 363 a.m.u.

$$\begin{bmatrix} \text{NH—COOCH}_3 \\ | \\ \text{M—N—COOCH}_3 \end{bmatrix}$$

EXAMPLE 2

2',2',2'-trichloroethyl-2β-thiohydrazodicarboxymethyl-α-isopropyenyl-4-oxo-3β-phenoxyacetamido-1-azetidine acetate.

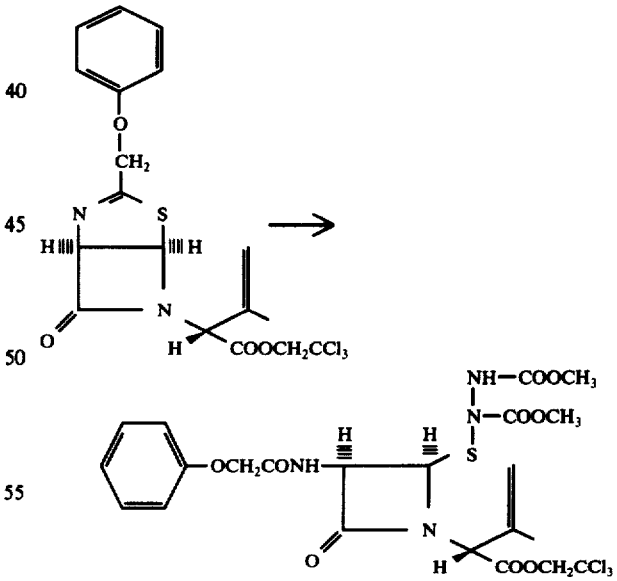

0.15 ml of water, 0.25 ml of methyl azodicarboxylate and 125 mg of p-toluenesulphonic acid monohydrate are added to a solution of 300 mg of 2',2',2'-trichloroethyl-α-isopropenyl-3-phenoxymethyl-1α,5α-thia-2,6-diaza-[3.2.0]-2-heptene-6-acetate-7-one in 10 ml of acetone. This is left for a total of 6 hours at room temperature, and then neutralized with a saturated solution of NaHCO₃, after which methylene chloride is added and it is shaken with salt water. The organic layer is collected over anhydrous Na₂SO₄ and evaporated. The residue is chromatographed over silica, eluting with 85/15 v/v benzene-ethyl acetate.

In this way, 320 mg of 2',2',2'-trichloroethyl-2β-thiohydrazodicarboxymethyl-α-isopropenyl-4-oxo-3β-phenoxyace-tamide-1-azetidine acetate are obtained, as an amorphous solid.

I.R. (CHCl$_3$): 3400 (n-H), 1770 (C = Oβ-lactam), 1740 (C = O ester and carbamates) and 1690 cm$^{-1}$ (C = O amide).

EXAMPLE 3

Methyl-2β-thiohydrazodicarboxyethyl-α-isopropylidene-4-oxo-3β-phenoxyacetamido-1-azetidine acetate.

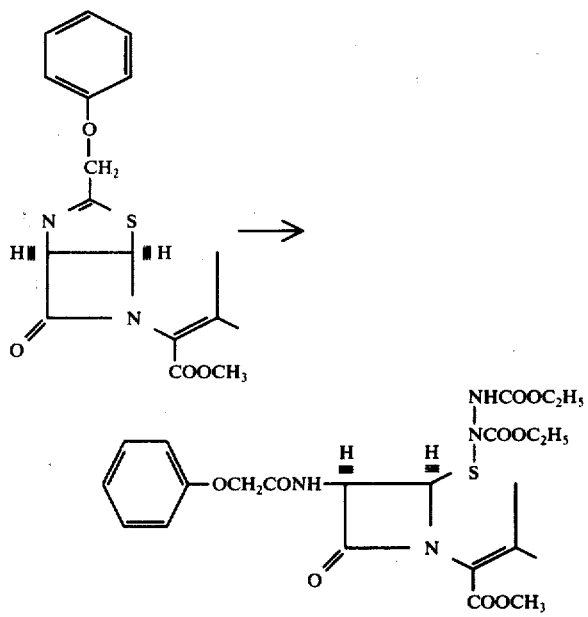

5 ml of water, 10 ml of ethyl azodicarboxylate and 10 g of p-toluenesulphonic acid monohydrate are added to a solution of 10 g of methyl-α-isopropylidene-3-phenoxymethyl-1α,5α-4-thia-2,6-diaza-[3,2,0]-2-heptene-6-acetate-7-one in 300 ml of acetone. This is left at room temperature for one night, and then neutralised with a saturated solution of NaHCO$_3$. The insoluble sodium salt of p-toluene-sulphonic acid which precipitates is filtered off. Then salt water and methylene chloride are added and the mixture shaken.

The dried organic layer is chromatographed over silica, eluting first with benzene to eliminate the unreacted azodicarboxylate and then with benzene-ethyl acetate (80:20) v/v.

In this way, 10.8 g of a white solid are obtained resulting from adding petroleum ether to a small volume solution of the product in benzene.

N.M.R. (CDCl$_3$): 1.21 (triplet, 6H, 2CH$_3$, C(H$_2$)), 2.12 and 2.28 (two s, 6H, (CH$_3$)$_2$C=), 3.77 (s, 3H, COOCH$_3$), 4.13 (q, 4H, 2CH$_2$—C(H$_3$)), 4.56 (s, 2H, O—CH$_2$—CO), 5.14 (dd, 1H, C(3) H), 5.86 (d, 1H, C(4)H) and 6.8 - 7.8 δ(m, 7H, C$_6$H$_5$ and amide 2NH).

I.R. (CHCl$_3$): 3410 (N - H) 1765 (C = Oβ-lactam) 1730 (C = O ester and carbamates) 1690 cm$^{-1}$ (C = O amide)

EXAMPLE 4

2',2',2'-trichloroethyl-2β-thiohydrazodicarboxyethyl-α-isopropylidene-4-oxo-3β-phenoxyacetamido-1-azetidine acetate.

A solution of 4.63 g of 2',2',2'-trichloroethyl-α-isopropylidene-3-phenoxymethyl-1α,5α-4-thio-2-,6-diaza-[3,2,0]-2-heptene-6-acetate-7-one in 200 ml of acetone containing 3 ml of ethyl azodicarboxylate, 3 ml of water and 1.91 g of p-toluenesulphonic acid monohydrate is left at room temperature for 24 hours. This is neutralised with NaHCO$_3$, thereafter CH$_2$Cl$_2$ and salt water are added, and the organic layer is separated. Upon chromatography over silica and eluting with benzene-ethyl acetate (95:5) v/v, the combined fractions give 6.0 g of the desired product.

N.M.R. (CDCl$_3$): 1.22 and 1.27 (two t, 6H, 2CH$_3$-C(H$_2$)), 2.22 and 2.37 (two s, 6H, (CH$_3$)$_2$C =), 3.9 - 4.5 (m, 4H, 2 CH$_2$ C(H$_3$)), 4.58 (s, 2H, O—CH$_2$—CO), 4.79 (dd, 2H, —O—CH$_2$—CCl$_3$), 5.10 (s, 1H, C(3)H), 5.98 (D, 1H, C(4)H), 6.64 (s, 2H, 2NH) and 6.8 - 7.5 δ (m, 5H, C$_6$H$_5$).

I.R. (CHCl$_3$): 3410 (N-H) 1760 (C = Oβ-lactam) 1730 (C = O ester and carbamate) and 1680 cm$^{-1}$ (C = O amide)

EXAMPLE 5

Methyl-2β-thiohydrazodicarboxymethyl-α-1'-methoxyethylidene-phenoxyacetamido-1-azetidine acetate.

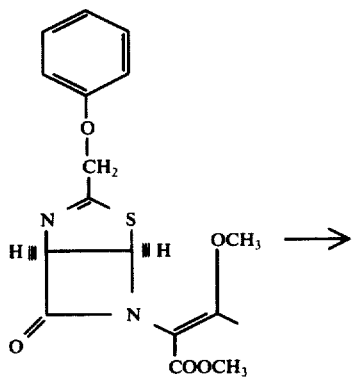

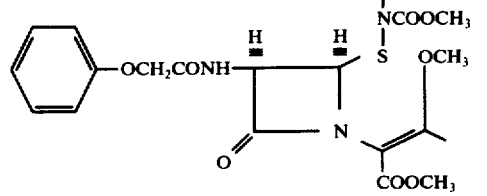

A solution of 0.500 g of methyl-α-1'-methoxyethylidene-3-phenoxymethyl-1α,5α-4-thio-2,6-diaza-[3,2,0]-2-heptene-6-acetate-7-one in 50 ml of acetone containing 0.5 ml of methyl azodicarboxylate, 3 ml of water and 50 mg of p-toluenesulphonic acid monohydrate is left at room temperature for 12 hours. This is neutralised with the equivalent quantity of NaHCO$_3$ and extracted with methylene chloride. The residue is chromatographed over silica, eluting with benzene-ethyl acetate (85:15) v/v.

In this way, 320 mg of the desired product are obtained.

IR (CHCl$_3$): 3420 (N - H) 1770 (C = 0β-lactam) 1730 (C = 0 ester and carbamates) 1680 (C = 0 amide)

Mass spectrum:

$$m/e\ 378\quad \begin{pmatrix} NH-COOCH_3 \\ | \\ M-NH-COOCH_3 \end{pmatrix}$$

$$m/e\ 148\quad \begin{pmatrix} NH-COOCH_3 \\ | \\ NH-COOCH_3 \end{pmatrix}^+$$

EXAMPLE 6

Methyl-7-phenoxyacetamido-3-methyl-3-cephem-4-carboxylate.

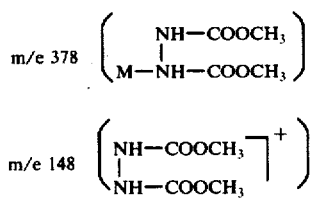

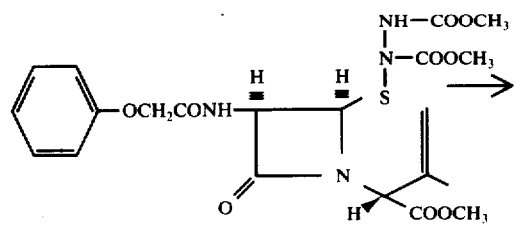

A solution of 1.0 g of methyl-2β-thiohydrazodicarboxymethyl-α-isopropenyl-4-oxo-3β-phenoxyacetamido-1-azetidine acetate in 40 ml of benzene is put on a magnetic stirrer with an excess of Al$_2$O$_3$ at room temperature. After 60 minutes a complete conversion occurs to the derivative methyl-7-phenoxyacetamido-3-methyl-3-cephem-4-carboxylate.

The Al$_2$O$_3$ is filtered off and the residue is crystallised from ethyl ether or chromatographed over silica, eluting with 90/10 v.v. benzene-ethyl acetate, to obtain 0.580 g of methyl-7-phenoxyacetamido-3-methyl-3-cephem-4-carboxylate; m.p. 140°-141° C (crystallised from ethyl ether).

I.R., N.M.R. in accordance with the literature (R.B. Morin: J. Am. Chem. Soc. 91; 1401 (1969)).

EXAMPLE 7

Methyl-7-phenoxyacetamido-3-methyl-3-cephem-4-carboxylate.

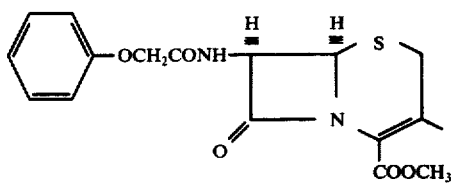

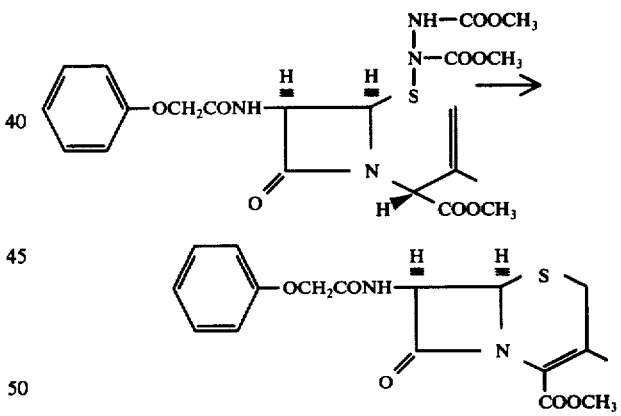

A solution of 400 mg of methyl-2β-thiohydrazodicarboxy-methyl-α-isopropenyl-4-oxo-3β-phenoxyacetamido-1-azetidinoacetate, in 30 ml of ethyl acetate, is put on magnetic stirrer in the presence of an excess of SiO$_2$ and heated under reflux for 48 hours. After filtering from the silica, it is evaporated and the residue crystallised or chromatographed over silica.

In this way, 180 mg of methyl-7-phenoxyacetamido-3-methyl-3-cephem-4-carboxylate are obtained; m.p. 141°-142° C.

I.R. and N.M.R. in accordance with data given in the literature. (R. B. Morin, J. Am. Chem. Soc. 91, 1969, p. 1401).

EXAMPLE 8

Methyl-7-phenoxyacetamido-3-methyl-3-cephem-4-carboxylate.

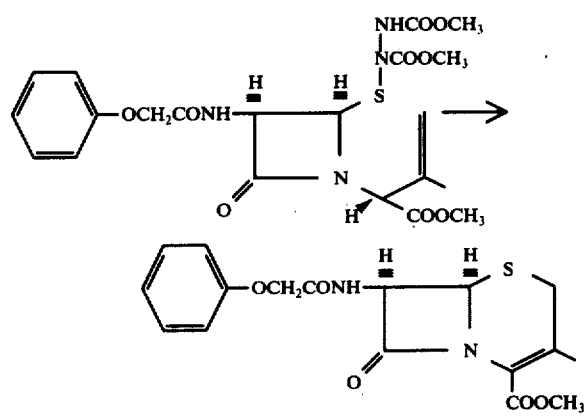

0.8 ml of a 30% aqueous solution of KOH are added under magnetic stirring and at room temperature to a solution of 510 mg of methyl-2β-thiohydrazodicarboxymethyl-α-isopropenyl-4-oxo-3β-phenoxyacetamido-1-azetidine acetate in 20 ml of benzene. This is left under stirring for 30 minutes, after which the organic layer is separated, washed with acidified water, then with water and finally dried.

The residue is crystallised from ethyl ether, giving 310 mg of methyl-7-phenoxyacetamido-3-methyl-3-cephem-4-carboxylate; m.p. 141°–142° C.

I.R. and N.M.R. in accordance with data reported in the literature. (R. B. Morin, J. Am. Chem. Soc. 91, 1401 (1969)).

EXAMPLE 9

2',2',2'-trichloroethyl-7-phenoxyacetamido-3-methyl-3-cephem-4-carboxylate.

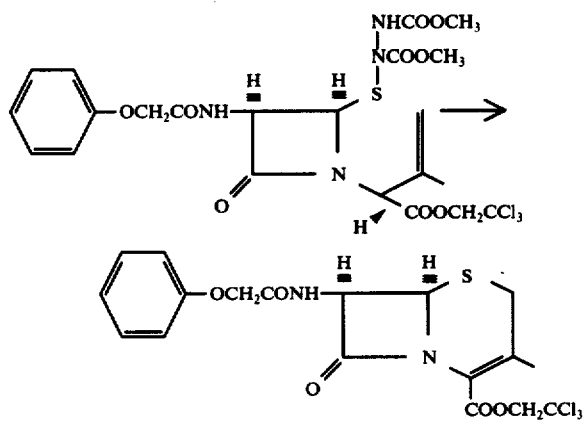

A solution of 250 mg of 2',2',2'-trichloroethyl-2β-thiohydrazodicarboxymethyl-α-isopropenyl-4-oxo-3β-phenoxyacetamido-1-azetidine-acetate in 15 ml of benzene is put under magnetic stirring at room temperature in the presence of an excess of $Al_2O_3$. This is left for 60 minutes, then filtered and chromatographed over silica, eluting with 93/7 v./v. benzene-ethyl acetate.

In this way, 150 mg of 2',2',2'-trichloroethyl-7-phenoxyacetamido-3-methyl-3-cephem-4-carboxylate are obtained; m.p. 116°–117° C.

I.R. and N.M.R. in accordance with data reported in the literature, (R. R. Chauvette, J. Org. Chem. 36, n.9, 1259 (1971)).

EXAMPLE 10

Methyl-7-phenoxyacetamido-3-methyl-3-cephem-4-carboxylate.

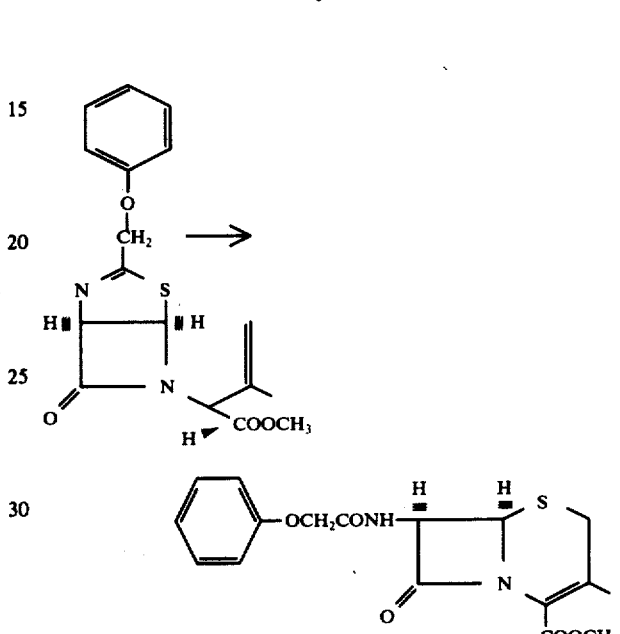

In this example a process is described for passing from (I) to (III), without isolating (II).

A solution of 500 mg of methyl-α-isopropenyl-3-phenoxymethyl-1α,5α,-4-thio-2,6-diaza-[3,2,0]-2-heptene-6-acetate-7-one in 25 ml of acetone with 0.5 ml of methyl azodicarboxylate, 250 mg of p-toluene-sulphonic acid monohydrate and 0.25 ml of water is left at room temperature for 6 hours. This is cooled to 0° C, the acid neutralised with a saturated solution of $NaHCO_3$, and extracted by shaking with benzene and salt water. The organic layer is dried over anhydrous $Na_2SO_4$, $Al_2O_3$ is added and it is left for 60 minutes at room temperature under magnetic stirring. It is filtered, the benzene is evaporated, and the residue crystallised from ethyl ether to give 350 mg of methyl-7-phenoxyacetamido-3-methyl-3-cephem-4-carboxylate; m.p. 140°–141° C.

I.R. and N.M.R. in accordance with data reported in the literature, (R. B. Morin, J. Am. Chem. Soc. 91, 1401 (1969)).

EXAMPLE 11

Methyl-7-phenoxyacetamido-3-methyl-3-cephem-4-carboxylate.

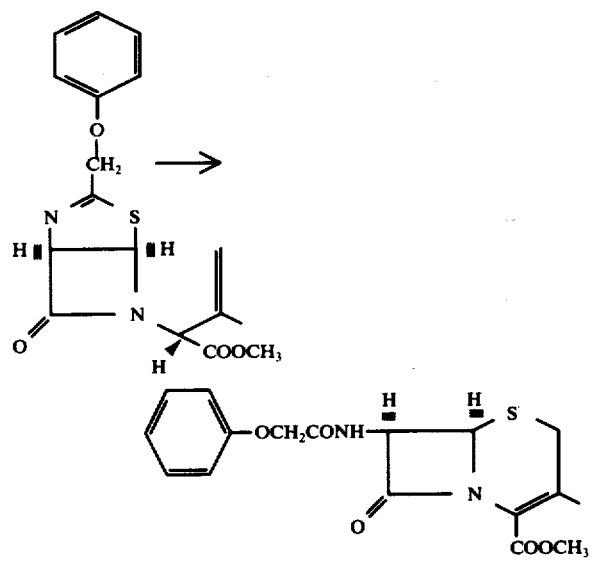

A solution of 750 mg of methyl-α-isopropenyl-3-phenoxymethyl-1α,5α,-4-thio-2,6-diaza-[3,2,0]-2-heptene-6-acetate-7-one in 35 ml of acetone, with 0.75 ml of methyl azodicarboxylate, 375 mg of p-toluenesulphonic acid monohydrate and 0.375 ml of water is left at room temperature for 6 hours. After cooling to 0° C this is neutralised with a saturated solution of NaHCO$_3$, water is added and it is then extracted with benzene.

The organic layer is dried, and 1.2 ml of a 30% solution of KOH are added under magnetic stirring at room temperature. After leaving for 30 minutes, the organic layer is separated, washed with acidified water, with water, and then dried over anhydrous Na$_2$SO$_4$. After evaporation, the residue is crystallised from ethyl ether, giving 540 mg of methyl-7-phenoxyacetamido-3-methyl-3-cephem-4-carboxylate; m.p. 141°-142° C.

I.R. and N.M.R. in accordance with data given in the literature (R. B. Morin, J. Am. Chem. Soc. 91, 1401 (1969)).

EXAMPLE 12 p-nitrobenzyl-7-[N-benzyloxycarbonyl-D-α-phenyl-glycinamido]-3-methyl-3-cephem-4-carboxylate.

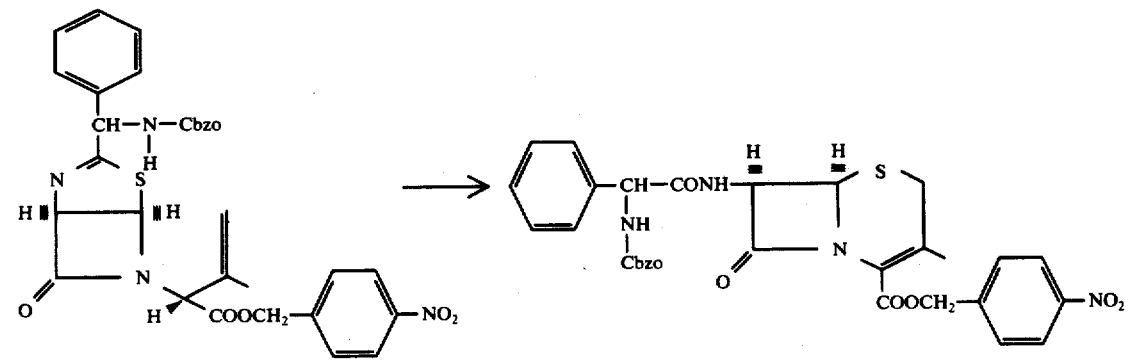

A solution of 600 mg of p-nitrobenzyl-α-isopropenyl-3-[N-benzyloxycarbonyl-benzylamine]-1α,5α,-2,6-diaza-[3,2,0]-2-heptene-6-acetate-7-one melting at 141°-143° C, in 20 ml of acetone containing 0.60 ml of methyl azodicarboxylate, 200 mg of p-toluenesulphonic acid monohydrate and 0.2 ml of water is left at room temperature for 20 hours. This is neutralised at 0° C with NaHCO$_3$, water is added and it is then extracted with benzene. It is then dried over anhydrous Na$_2$SO$_4$ and the solution is put under magnetic stirring at room temperature with 0.2 ml of a 30% KOH solution and left for 60 minutes. Finally the organic layer is separated, washed with acidified water, then with water, and dried over anhydrous Na$_2$SO$_4$ giving a residue which, upon crystallization from ether, gives 230 mg of p-nitrobenzyl-7-[N-benzyloxy-carbonyl-D-α-phenyl-glycinamido]-3-cephem-4-carboxylate; m.p. 198°- 202° C.

I.R. and N.M.R. in accordance with data obtained from a sample prepared by another method.

EXAMPLE 13

Methyl-7-phenoxyacetamido-3-methyl-3-cephem-4-carboxylate (See Example 6).

A solution of 1.0 g of methyl-2β-thiohydrazodicarboxyethyl-α-isopropenyl-4-oxo-3β-phenoxyacetamido-1-azetidine acetate in 10 ml of anhydrous tetrahydrofuran is added to a suspension of 5 equivalents of lithium methoxide in 30 ml of anhydrous tetrahydrofuran at −40° C, and the resulting mixture is stirred for 1 hour. After neutralization with acetic acid, the solution is warmed up to room temperature, neutralized with an aqueous solution of sodium bicarbonate, and extracted with ethylacetate.

The organic layer is washed with water, dried over anhydrous sodium sulphate, and the solvent evaporated in vacuo, to give methyl-7-phenoxyacetamido-3-methyl-3-cephem-4-carboxylate which is then crystallized from diethyl ether.

I.R. and N.M.R. in accordance with data reported in the literature (R. B. Morin, J. Am. Chem. Soc. 91, 1401 (1969)).

EXAMPLE 14

The following compounds were obtained in a manner analogous to that described above.

a. 2',2',2'-trichloroethylester of 7-phenylacetamido-3-methyl-3-cephem-4-carboxylic acid; m.p. 163° C.

b. p-methoxybenzylester of 7-phenylacetamido-3-methyl-3-cephem-4-carboxylic acid; m.p. 151°-152° C.

c. p-chlorophenacylester of 7-phenoxyacetamido-3-methyl-3-cephem-4-carboxylic acid; m.p. 176° C.

d. phenacylester of 7-phenylacetamido-3-methyl-3-cephem-4-carboxylic acid; m.p. 190°–191° C.

e. p-bromophenacylester of 7-phenylacetamido-3-methyl-3-cephem-4-carboxylic acid; m.p. 196°–198° C.

f. t-butylester of 7-phenylacetamido-3-methyl-3-cephem-4-carboxylic acid; m.p. 122° C.

g. p-nitrobenzylester of 7-phenoxyacetamido-3-methyl-3-cephem-4-carboxylic acid; m.p. 191°–193° C.

h. methylester of 7-phenylacetamido-3-methyl-3-cephem-4-carboxylic acid; m.p. 188°–190° C.

i. p-nitrobenzylester of 7-(thiophene-2-acetamido)-3-methyl-3-cephem-4-carboxylic acid; m.p. 217° C.

j. p-methoxybenzylester of 7-(thiophene-2-acetamido)-3-methyl-3-cephem-4-carboxylic acid; m.p. 160° C.

EXAMPLE 15

Methyl-2β-thiohydrazodicarboxyethyl-α-[3'-acetoxy-1'-isopropenyl]-4-oxo-3β-acetamino-1-azetidino acetate

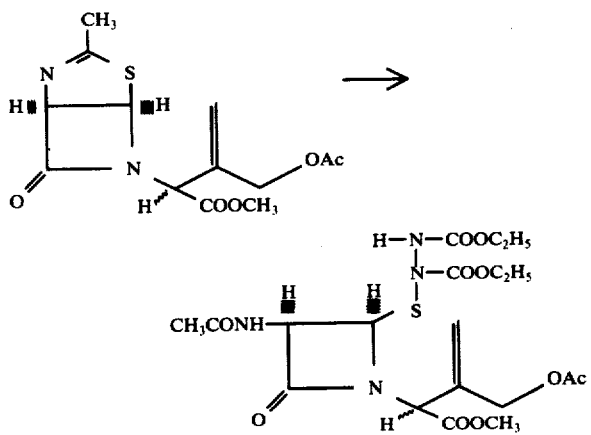

A solution of 0.8 g of methyl-α-[3'-acetoxy-1'-isopropenyl]-3-methyl-1α,5α-4-thia-2,6-diaza-[3,2,0]-2-heptene-6-acetate-7-one (a mixture of two epimers) in 30 ml of acetone containing 0.8 ml of ethyl azodiacarboxylate, 0.3 ml of water and 0.5 g of p.toluenesulfonic acid monohydrate, is kept at room temperature for 2 hours. It is then neutralized with NaHCO₃ and the product extracted with ethyl acetate. The organic layer is dried over anhydrous Na₂SO₄ and the solvent evaporated in vacuo. The residue is chromatographed over silica eluted with benzene/ethylacetate 60:40 v/v to give 0.6 g of the desired compound as a mixture of two epimers.

N.M.R. (CDCl₃): 2.06 and 2.09 (two s, CH₃COO— and CH₃CONH—), 3.80 and 3.82 (two s, CH₃O), 4.75 and 4.95 (two m, = CH₂), 5.29–5.60 (two broad d, β-lactam protons).

EXAMPLE 16

Methyl-2β-thiohydrazodicarboxyethyl-α-[3'-acetoxy-1'-isopropenyl]-4-oxo-3β-trimethylacetamido-1-azetidino-acetate.

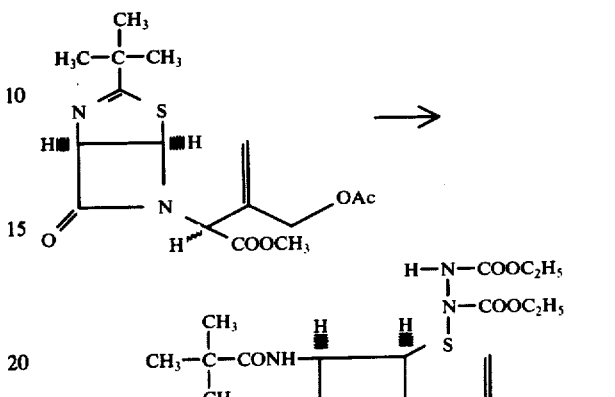

A solution of 0.750 g of methyl-α-[3'-acetoxy-1'-isopropenyl]-3-tert.butyl-1α,5α-4-thia-2,6-diaza-[3,2,0]-2-heptene-6-acetate-7-one (a mixture of two epimers) in 10 ml of acetone containing 0.750 ml of ethyl azodicarboxylate, 0.2 ml of water and 0.390 g of p.toluenesulfonic acid monohydrate, is kept at room temperature for 24 hours. After neutralization with NaHCO₃, the product is extracted with ethyl acetate and the organic layer dried over anhydrous Na₂SO₄. The solvent is evaporated in vacuo and the residue is chromatographed over silica eluted with benzene/ethyl acetate 70:30 v/v to give 0.5 g of the desired compound as a mixture of two epimers.

EXAMPLE 17

Methyl-7-acetamido-3-acetoxymethyl-3-cephem-4-carboxylate

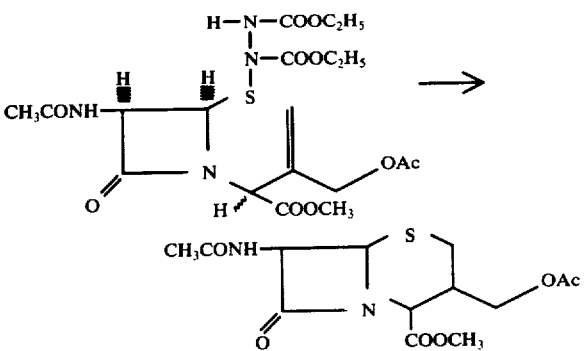

A solution of 0.5 g of methyl-2β-thiohydrazodicarboxyethyl-α-[3'-acetoxy-1'-isopropenyl]-4-oxo-3β-acetamido-1-azetidino-acetate in 15 ml of dimethylformamide and 5 ml of tetrahydrofurane, is cooled to −78° C and treated with 1.1 g of potassium tert.butoxide. After stirring for 20 minutes, the reaction mixture is quenched with acetic acid, diluted with water, and extracted with ethyl acetate. The solvent is evaporated in vacuo, and the residue chromatographed on silica eluted with benzene/ethylacetate 70:30 v/v to give 0.180 g of methyl-7-acetamido-3-acetoxymethyl-cephem-4-carboxylate as a mixture of Δ² and Δ³ isomers. See D.O. SPRY, J.A.C.S. 92, 5006 (1970).

EXAMPLE 18

Methyl-7-trimethylacetamido-3-acetoxymethyl-3-cephem-4-carboxylate.

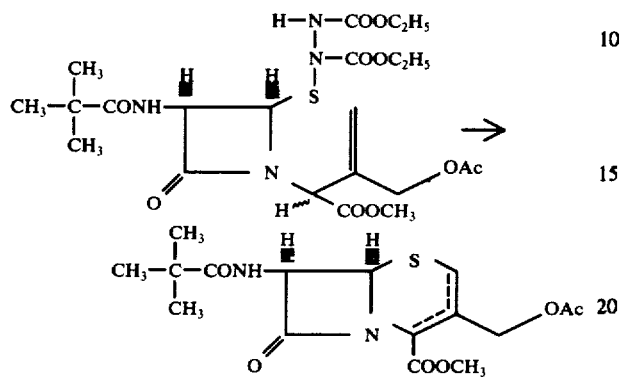

A solution of 0.850 g of methyl-2α-thiohydrazodicarboxyethyl-α-[3′-acetoxy-1′-isopropenyl]-4-oxo-3β-trimethylacetamido-1-azetidino-acetate in 15 ml of dimethylformamide and 3 ml of tetrahydrofurane, is cooled to −70° C and treated with 1.2 g of potassium tert.butoxide. After stirring for 15 minutes, the reaction mixture is quenched with acetic acid, diluted with water, and extracted with ethyl acetate. The solvent is evaporated in vacuo, and the residue chromatographed on silica eluting with benzene/ethyl acetate 80:20 v/v to give 0.190 g of methyl-7-trimethylacetamido-3-acetoxy-methyl-cephem-4-carboxylate as a mixture of Δ² and Δ³ isomers.

N.M.R. (CDCl₃) : 2.08δ (s, CH₃CO), 3.51δ (dd, C(2)H₂), 3.83 and 3.90δ (two s, CH₃O), 4.69δ (s, C(4)H), 4.87 and 5.30δ (two d, C(6)H), 5.62 and 5.82δ (two dd, C(7)H), and 6.50δ (broad s, =C (2) H).

What is claimed is:

1. A process for preparing a cephalosporin of structure:

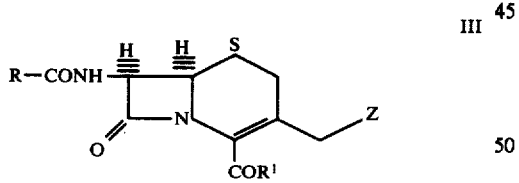

III where R is selected from the class consisting of hydrogen, alkyl having from 1 to 4 carbon atoms, cyanomethyl-, thienyl-methyl-, naphthyl-methyl-, phenyl-methyl-, phenoxy-methyl-, phenyl-isopropyl-, phenoxy-isopropyl-, pyridyl-4-thiomethyl-, and tetrazolyl-1-methyl-;

R¹ is selected from the class consisting of a hydroxyl, alkoxy having from 1 to 4 carbon atoms, trichloroethoxy-, benzyloxy-, p-methoxy-benzyloxy-, p-nitrobenzyloxy-, benzhydryloxy-, triphenylmethoxy-, phenacyloxy-, and p-halophenacyloxy;

Z is selected from the class consisting of hydrogen, —O—alkyl, —O—CO—alkyl, —Br, —I, —N₃, —NH₂, —O—CO—CH₃, —O—CO—NH₂, and 2-mercapto-5-methyl-1,3,4-thiadiazole;

wherein a compound of structure

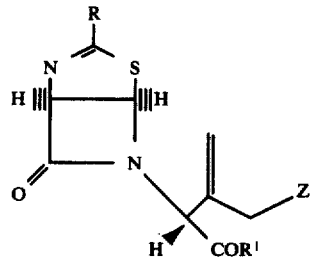

(I′)

dissolved in acetone or tetrahydrofuran is reacted at a temperature between −20° C and +80° C in the presence of p-toluenesulphonic, sulphuric, trifluoroacetic, formic or oxalic acid, with an azoderivative of the formula

wherein R² and R³ are the same or different and represent CN—, or the radicals —COR⁴, —COOR⁴,

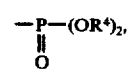

—CONHR⁴, where R₄ is a lower alkyl having from 1 to 4 carbon atoms, to give a compound of the structure:

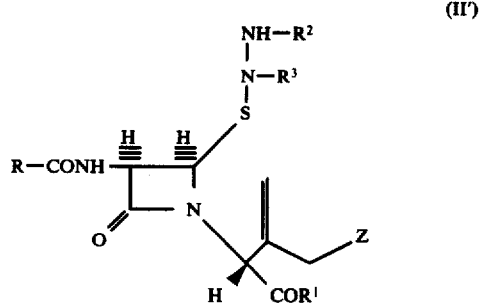

(II′)

in which R, R¹, R², R³ and Z have the meanings given above, and said intermediate (II′), dissolved in benzene, ethyl acetate or dimethylformamide, is reacted at a temperature between −100° C and +120° C with an aluminum or silicon oxide or with potassium or sodium hydroxide, potassium tert. butoxide or lithium methoxide, to finally give the desired compound (III) which is isolated and purified in known manner.

2. A process as claimed in claim 1, wherein a compound of structure

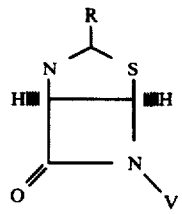

(I)

dissolved in acetone or tetrahydrofuran is reacted at a temperature between −20° C and +80° C in the presence of p-toluenesulphonic acid with an azo- derivative of the formula:
to give a compound of the formula:
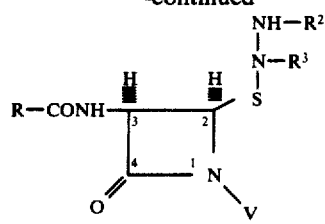
(II)
where V may be hydrogen, or the residues:
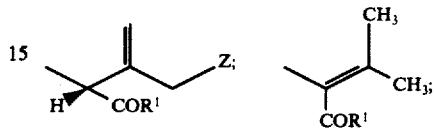
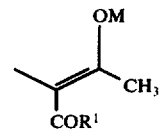
where R, R$^1$, R$^2$, R$^3$, and Z have the meanings given in claim 1, and M is an alkyl group having from 1 to 4 carbon atoms.
* * * * *